United States Patent [19]
Odashima et al.

[11] Patent Number: 4,473,504

[45] Date of Patent: Sep. 25, 1984

[54] METHOD OF PRODUCING GRANULAR METALLIC SOAP

[75] Inventors: Osamu Odashima, Amagasaki; Osamu Kondo, Kyoto, both of Japan

[73] Assignee: Shinto Paint Co., Ltd., Amagasaki, Japan

[21] Appl. No.: 286,540

[22] Filed: Jul. 24, 1981

[30] Foreign Application Priority Data

Jul. 30, 1980 [JP] Japan ................................. 55-105696

[51] Int. Cl.$^3$ ............................................... C11C 1/00
[52] U.S. Cl. ..................................... 260/414; 260/413
[58] Field of Search .............................. 260/414, 413 S

[56] References Cited

U.S. PATENT DOCUMENTS

| 3,446,749 | 3/1969 | Weisfeld et al. | ................. 260/414 X |
| 3,476,786 | 11/1969 | Lally et al. | ...................... 260/414 X |
| 3,519,571 | 7/1970 | Szczepanek et al. | ........... 260/414 X |
| 3,803,188 | 4/1974 | Scott et al. | ...................... 260/414 X |
| 4,060,535 | 11/1977 | Cinco | ................................. 260/414 |

FOREIGN PATENT DOCUMENTS

| 149409 | 4/1950 | Australia | ............................. 260/414 |
| 889256 | 2/1962 | United Kingdom | ................ 260/414 |

Primary Examiner—Thomas A. Waltz
Attorney, Agent, or Firm—Armstrong, Nikaido, Marmelstein & Kubovcik

[57] ABSTRACT

This invention relates to a method of producing large granules of metallic soap by reacting a water-insoluble metal carbonate and fatty acid.

3 Claims, No Drawings

METHOD OF PRODUCING GRANULAR METALLIC SOAP

The present invention relates to a method of producing granular metallic soap, and more particularly to a method of producing granular metallic soap characterized in that a water-insoluble metal carbonate and a fatty acid, in a water-dispersed state, are reacted by heating the dispersion at a temperature above the temperature at which the fatty acid begins to melt but below the melting point of the metallic soap to be formed.

Metallic soaps are well known and have been widely used in the industries of resins, paints, papers, fibers, greases, etc. as stabilizers, lubricants, water-repellents, thickeners, coating agents, etc. In addition to such uses, metallic soaps are used as catalysts in chemical reactions, and also as additives for rubber to improve adhesiveness or bonding of the rubber with steel cords.

The methods heretofore known for industrial production of metallic soap include two methods. One of them is the so-called double decomposition method wherein a water-soluble metal salt, such as a chloride or sulfate of a metal, and an alkali-metal salt of a fatty acid are ion-reacted in an aqueous solution state to produce water-insoluble metallic soap. The advantage of this method is that the reaction proceeds easily at a relatively low temperature of from room temperature to about 70° C., and that a high-purity product can be obtained by washing the resulting metallic soap with water. Therefore, this method is the most general method for producing metallic soap for which high-purity is required. However, since the metallic soap by this method is obtained in an extremely fine powder form, there will be a loss due to flying upon handling, depending on its uses, and also there is a need to prevent pollution of operation environment. For this reason, the metallic soap is used after addition of a suitable wetting agent or after being formed into flakes or granules. The other method of producing metallic soap is the so-called fusion process, in which a metal oxide, hydroxide or carbonate and a fatty acid are reacted by fusing them at a temperature above the melting point of the metallic soap to be formed, and by-produced water or carbon dioxide gas is expelled out of the reaction system, whereby the metallic soap is taken out in a molten state. The advantage of this method is that the method is simpler than the above-mentioned double decomposition method since the reaction vessel can be of a small type and the water-washing and drying operations can be dispensed with. However, since the reaction is carried out at a high temperature above the melting point of the metallic soap to be formed, generally at about 130° C., undesirable side reactions will occur to interfere with obtaining high-purity products, so that this method has not been used so generally as the double decomposition method.

The present invention is based on out discovery that metallic soap can be obtained in granular form under particular reaction conditions which have not been anticipated from the above-mentioned, heretofore known methods. That is to say, the present invention has made it possible to produce granular metallic soap in high yields by reacting a water-insoluble metal carbonate and a fatty acid, in a water-dispersed state, at a temperature above the temperature at which the fatty acid begins to melt and below the melting point of the metallic soap to be formed. The reaction temperature of the present invention is characterized in that it is much lower than that of the conventional melting or fusion method. Surprisingly, in addition to the fact that the metallic soap obtained according to the method of the present invention is of high purity, it is obtained as porous granules which are different from the metallic soap in fine powder form obtained by the conventional double decomposition method. In the present invention, the metallic soap formed upon the completion of the reaction precipitates or separates out in granular form in the upper layer of the reaction system. Accordingly, after filtering it off, followed only by water-washing and drying, there can be obtained a product which is free from any problem of flying. Moreover, not only the water-washing and drying can be easily performed, but also there is no need of granulating the product anew.

In the following, the present invention is explained in more detail.

The water-insoluble metal carbonates to be used in the present invention can be industrial products available on the market. Among such carbonates, carbonates of zinc, cobalt, iron, nickel, manganese, lead, copper and magnesium may be used, cobalt being most preferable. Further it is preferable to use those carbonates that are as new as possible after production. In a practical method of carrying out the present invention, an alkali-carbonate or acid alkali-carbonate is added to an aqueous solution of a water-soluble metal salt, for example chloride, sulfate or nitrate of the above mentioned metal, and the resulting aqueous dispersion of the water-insoluble carbonate can be used as such for the reaction with fatty acid. As the fatty acid, any can be used which is solid at room temperature and whose temperature at which it begins to melt is lower than the boiling point of water used as the dispersion medium of the reaction liquid. For example, lauric acid, stearic acid, palmitic acid, behenic acid, myristic acid, etc. may be used. Among them stearic acid is most preferable.

There is no particular restriction on the quantitative ratio between the water-insoluble metal carbonate and fatty acid to be reacted, but in general, the use of them in chemical equivalents is preferable. Depending on the use purposes of the metallic soap, an excess quantity of fatty acid may be used. The quantity of water use as the dispersion medium of the reaction system is not critical so far as the quantity permits stirring throughout the whole reaction period. For example, a quantity of water more than ten times, preferably more than 20 times, as much as the weight of the water-insoluble metal carbonate used is suitable. In carrying out the reaction, the water-insoluble metal carbonate and fatty acid may be stirred and dispersed in water beforehand, without the use of any surface-active agent, emulsifier, etc. and heated to a temperature within the temperature range prescribed above. It is also possible to react them by heating an aqueous dispersion of the water-insoluble metal carbonate to the predetermined temperature, followed by addition of fatty acid.

The reaction temperature according to the present invention lies within the temperature range above the temperature at which the fatty acid used begins to melt and below the melting point of the resulting metallic soap. At a temperature below this temperature range, the metal carbonate and fatty acid in a water-dispersed state do not react with each other. Also, at a temperature above this temperature range, the metallic soap formed with the passage of time will be melted and fused together with unreacted fatty acid to form a viscous oil layer, and the reaction does not come to completion. Within the temperature range of the present invention, the reaction temperature may be varied at will. For example, in the case where a fatty acid which begins to melt at 58° C. is used and the melting point of the resulting metallic soap is 94° C., the reaction may be completed at a constant temperature, for example at 70° C., or may be completed at any proper temperature within the range of from 58° C. to 94° C., for example under temperature elevation of from 63° C. to about 75° C. However, practically it is desirable to avoid a high-temperature reaction as scrupulously as possible, in order not to lower the purity of the metallic soap to be obtained.

When the water-insoluble metal carbonate and fatty acid, in a water-dispersed state, are stirred and heated to the temperature range according to the present invention, the reaction will proceed, and granular metallic soap dispersed in water will be formed, while generating carbon dioxide gas. Upon the termination of the reaction when the metal carbonate in the reaction system is disappeared and the generation of bubbles of by-produced carbon dioxide gas is no longer observed, the heating is stopped, and the metallic soap floating on the upper layer of the reaction liquid is filtered off, washed with water and dried. The metallic soap obtained itself is in the form of porous granules, so that it constitutes a product which is free from any concern of flying away. Therefore, this method is very advantageous from the industrial viewpoint.

In the following, examples of practice of the present invention will be explained.

EXAMPLE 1

15.4 g cobalt carbonate in powder form (containing 8.0 g cobalt) and 78 g stearic acid (melt initiating temperature 58° C.) in powder form were heated while they were dispersed under stirring in 800 ml water, and were caused to react at a constant temperature of 65° C. After 20 minutes, bubbles which were generated vigorously at the early stage of the reaction became scarcely observed. At that temperature, stirring was further continued for 30 minutes, and thereafter the heating was stopped. Cobalt stearate which was generated in the upper layer of the reaction liquid was filtered off, washed with 400 ml water and dried at 60° C. 8.5 g of granular cobalt stearate (melting point 94° C.) having an average grain diameter of about 1 mm was obtained. The cobalt content of this product was 9.1% and the yield relative to the cobalt used was 97%.

EXAMPLE 2

To an aqueous solution of zinc chloride prepared by dissolving 22 g zinc chloride (containing 47.8% zinc) in 33 ml water, 300 g of a 9% aqueous acid sodium carbonate solution was added under stirring to produce an aqueous zinc carbonate dispersion containing 10.5 g zinc. This liquid was heated under stirring, and when the temperature reached 65° C., addition of granular stearic acid (melt initiating temperature 56° C.) was started. While the temperature was elevated over a 15-minute period, 90 g was added. When the addition was terminated, the temperature of the liquid was 72° C. Under slow heating, the reaction was continued for 40 minutes. When the reaction was accomplished, the temperature of the liquid was 76° C. Heating was then stopped, and zinc stearate generated in the upper layer of the reaction liquid was filtered off. It was washed with water 3 times, the quantity of water used for each time being 1000 ml. Thereafter, it was dried at 105° C. to obtain 100 g granular zinc stearate (melting point 120° C.) having an average grain diameter of about 1 mm. The zinc content of this product was 10.38%, and the yield relative to the zinc used was 98.9%.

EXAMPLE 3

To an aqueous solution of cobalt chloride prepared by dissolving 239 g cobalt chloride hydrate (containing 24.4% cobalt) in 2700 ml water, 1313 g of a 80% aqueous sodium carbonate solution was added under stirring to produce an aqueous cobalt carbonate dispersion containing 58.3 g cobalt. This liquid was heated under stirring, and at a constant temperature of 55° 1 C., 452 g myristic acid (melt initiating temperature 50° C.) in scale form was added over a period of 15 minutes. Stirring was continuted for an additional period of 60 minutes while the temperature was held constant at 55° C. Thereafter, heating was stopped. Cobalt myristate formed in the upper layer of the reaction liquid was filtered off. It was washed with water in the same way as in Example 2, and was dried at 60° C. to obtain 508 g granular cobalt myristate (melting point 90° C.) having an average grain diameter of about 0.8 mm. The cobalt content of this product was 11.35%, and the yield of the product based on the cobalt used was 98.9%.

The metallic soap thus obtained according to this invention is useful for any known application wherein conventional metallic soaps have been used. Particularly, however, the metallic soap of this invention is useful as an additive to natural or synthetic rubber to improve its adhesiveness or bonding with steel cords for use in steel radial tires.

What we claim is:

1. A method of producing granular metallic soap characterized in that a water-insoluble metal carbonate and a fatty acid, in a water-dispersed state, are reacted by heating the dispersion at a temperature above the temperature at which the fatty acid begins to melt but below the melting point of the metallic soap to be formed until the metal carbonate in the reaction system has disappeared and the generation of bubbles of by-produced carbon dioxide gas is no longer observed, stopping the heating, recovering the resultant metallic soap in the form of porous granules by filtration, washing the metallic soap with water and then drying the same.

2. A method according to claim 1 wherein the metal is cobalt.

3. A method according to claim 1 wherein the fatty acid is stearic acid.

* * * * *